United States Patent
Bar-El et al.

(10) Patent No.: US 11,020,525 B2
(45) Date of Patent: Jun. 1, 2021

(54) INJECTOR CARTRIDGE DOOR LOCKING MECHANISM

(71) Applicant: West Pharma. Services IL, Ltd., Ra'anana (IL)

(72) Inventors: Yossi Bar-El, Beit Arye (IL); Gil Yigal, Gan Yavne (IL); Michael Yudelevich, Winnipeg (CA)

(73) Assignee: WEST PHARMA. SERVICES IL, LTD., Ra'anana (IL)

(*) Notice: Subject to any disclaimer, the term of this patent is extended or adjusted under 35 U.S.C. 154(b) by 0 days.

(21) Appl. No.: 16/637,100

(22) PCT Filed: Aug. 3, 2018

(86) PCT No.: PCT/US2018/045149
§ 371 (c)(1),
(2) Date: Feb. 6, 2020

(87) PCT Pub. No.: WO2019/032395
PCT Pub. Date: Feb. 14, 2019

(65) Prior Publication Data
US 2020/0246538 A1    Aug. 6, 2020

Related U.S. Application Data

(60) Provisional application No. 62/543,894, filed on Aug. 10, 2017.

(51) Int. Cl.
*A61M 5/145* (2006.01)
*A61M 5/142* (2006.01)

(52) U.S. Cl.
CPC .... *A61M 5/14566* (2013.01); *A61M 5/14248* (2013.01)

(58) Field of Classification Search
CPC .. A61M 5/145; A61M 5/142; A61M 5/14566; A61M 2205/6045; A61M 5/145573; A61M 5/1458
See application file for complete search history.

(56) References Cited

U.S. PATENT DOCUMENTS

2017/0043092 A1* 2/2017 Murakami .............. A61M 5/20

FOREIGN PATENT DOCUMENTS

JP    2015536696 A    12/2015
JP    2016507290 A    3/2016
(Continued)

OTHER PUBLICATIONS

International Search Report and Written Opinion dated Nov. 15, 2018 in International Appl. No. PCT/US2018/045149.
(Continued)

*Primary Examiner* — Deanna K Hall
(74) *Attorney, Agent, or Firm* — Panitch Schwarze Belisario & Nadel LLP (57) ABSTRACT

An injector includes an injector housing and a cartridge door movably mounted to the injector housing between a fully closed position and an open position. A latching mechanism is movable between a latched position, locking the cartridge door to the injector housing in the fully closed position thereof, and an unlatched position, unlocking the cartridge door from the injector housing, thereby enabling movement of the cartridge door toward the open position. The latching mechanism is oriented in the unlatched position when the cartridge door is empty and the latching mechanism is configured to move to the latched position solely when a cartridge is present in the cartridge door and the cartridge door is subsequently moved to the fully closed position thereof.

7 Claims, 6 Drawing Sheets

(56) References Cited

FOREIGN PATENT DOCUMENTS

| | | |
|---|---|---|
| WO | 2014052676 A1 | 4/2014 |
| WO | 2014111332 A1 | 7/2014 |
| WO | 2015018787 A1 | 2/2015 |

OTHER PUBLICATIONS

Office Action dated Jul. 14, 2020 in Japanese Application No. 2020-507100.

* cited by examiner

INJECTOR CARTRIDGE DOOR LOCKING MECHANISM

CROSS-REFERENCE TO RELATED APPLICATIONS

This application is a Section 371 of International Application No. PCT/US2018/045149, filed Aug. 3, 2018, which was published in the English language on Feb. 14, 2019, under International Publication No. WO 2019/032395 A1, which claims the benefit of priority under 35 U.S.C. § 119(e) from U.S. Provisional Patent Application No. 62/543,894, titled "Bay Door Lock Only With Cartridge", filed Aug. 10, 2017, the entire contents of each of which are incorporated herein by reference in their entirety.

BACKGROUND OF THE DISCLOSURE

The present disclosure is generally directed to a cartridge loaded injector, and, more particularly, to a cartridge loaded injector having an injector door locking mechanism that requires the presence of the cartridge within the injector to activate the door lock.

An injector, such as, for example, a drug injector, is typically loaded by a user with a cartridge containing therein a substance, e.g., a medicament or drug, to be dispensed. In many conventional injectors, an injector door is permanently locked when closed after the cartridge has been, or should have been, loaded. In some instances, the door is inadvertently pushed closed and locked during delivery to the user, without a cartridge having been loaded therein. In other instances, users have inadvertently closed the door prematurely, before inserting the cartridge. Once an injector door is closed and permanently locked without a cartridge loaded therein, the injector is effectively rendered inoperable. Premature closing and locking of the injector door, prior to insertion of a cartridge into the injector, may result in delaying a user from receiving a medication at the necessary time. Additionally, premature closing and locking of the injector door, prior to insertion of a cartridge into the injector, may force the user to unnecessarily purchase another injector.

To address this problem, some injectors employ a door blocking mechanism to prevent closing of the door until the cartridge has been inserted. Some users may perceive blocking of the door, however, (when no cartridge has been inserted) as merely the door requiring the exertion of a greater amount of force to close the door, which may damage the injector. Alternatively, the injector door may be forced closed during delivery to the user, which may also damage the injector. For example, forcing the injector door closed may bend or break various components of the injector, rendering the injector inoperable, and, therefore, ultimately arriving at the same inoperable state of a prematurely locked injector. Other injectors employ a mechanism to unlock a closed injector door to counter the problem of premature injector door closing. Allowing a locked injector door to be reopened, however, may lead to inadvertent unlocking of the door after the cartridge has been inserted. This occurrence may lead to various problems that permanent locking of the injector door was intended to address.

Therefore, it would be advantageous to manufacture an injector having an injector door locking mechanism that requires the presence of the cartridge within the injector to activate the door lock.

BRIEF SUMMARY OF THE DISCLOSURE

Briefly stated, one aspect of the present disclosure is directed to an injector configured to receive therein a cartridge containing a substance to be dispensed. The injector includes an injector housing and a cartridge door movably mounted to the injector housing and having an open end and an interior channel to load the cartridge therein through the open end. The cartridge door is movable between a fully closed position, wherein the open end is obscured by the injector housing to prevent insertion of the cartridge into the interior channel, and an open position, wherein the open end is sufficiently exposed to receive the cartridge therethrough and into the interior channel. A latching mechanism is movable between a latched position, locking the cartridge door to the injector housing in the fully closed position thereof, and an unlatched position, unlocking the cartridge door from the injector housing, thereby enabling movement of the cartridge door toward the open position. The latching mechanism is oriented in the unlatched position when the cartridge door is empty and the latching mechanism is configured to move to the latched position solely when a cartridge is present in the cartridge door and the cartridge door is subsequently moved to the fully closed position thereof.

BRIEF DESCRIPTION OF THE DRAWINGS

The following detailed description of aspects of the disclosure will be better understood when read in conjunction with the appended drawings. It should be understood, however, that the invention is not limited to the precise arrangements and instrumentalities shown. In the drawings.

DETAILED DESCRIPTION OF THE DISCLOSURE

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the injector, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1A-4 an injector, generally designated 10, in accordance with an embodiment of the present disclosure. In the illustrated embodiment, the injector 10 takes the form of a wearable injector (patch injector), such as, for example, without limitation, a wearable drug injector, but the disclosure is not so limited.

As should be understood by those of ordinary skill in the art, the injector 10 generally includes a housing 12 having a first surface 14 configured to contact a skin surface of a user (not shown), e.g., a patient, the first surface 14 having an opening 14a therein. In the illustrated embodiment, the first surface 14 defines a base surface of the injector housing 12, but the disclosure is not so limited. The housing 12 also includes a second surface (not shown) opposing the first surface 14, e.g., a top, external surface of the injector housing 12, but the disclosure is not so limited. As also should be understood by those of ordinary skill in the art, an injection needle (not shown) is movably mounted within the injector housing 12 and is translatable between a retracted position, wherein at least a tip of the injection needle is contained within the injector housing 12, and an injection position, wherein at least the tip of the injection needle protrudes from the injector housing 12 through the opening 14a and into the skin of a user (not shown).

The injector 10 is configured to receive therein a sealed cartridge 50 (FIG. 3A), e.g., a generally cylindrical cartridge 50 having a distal neck portion, containing a substance (not shown), e.g., medicament. The cartridge 50 is sealed at one end by a piston 50a and at another end by a pierceable septum 50b. After (or during) insertion of the cartridge 50 into the injector 10, the cartridge 50 is unsealed and fluidly connected to the injection needle, in a manner well understood by those of ordinary skill in the art (via piercing of the septum 50b), to dispense the substance within the cartridge 50 through the injection needle to a user.

Figure 1A:
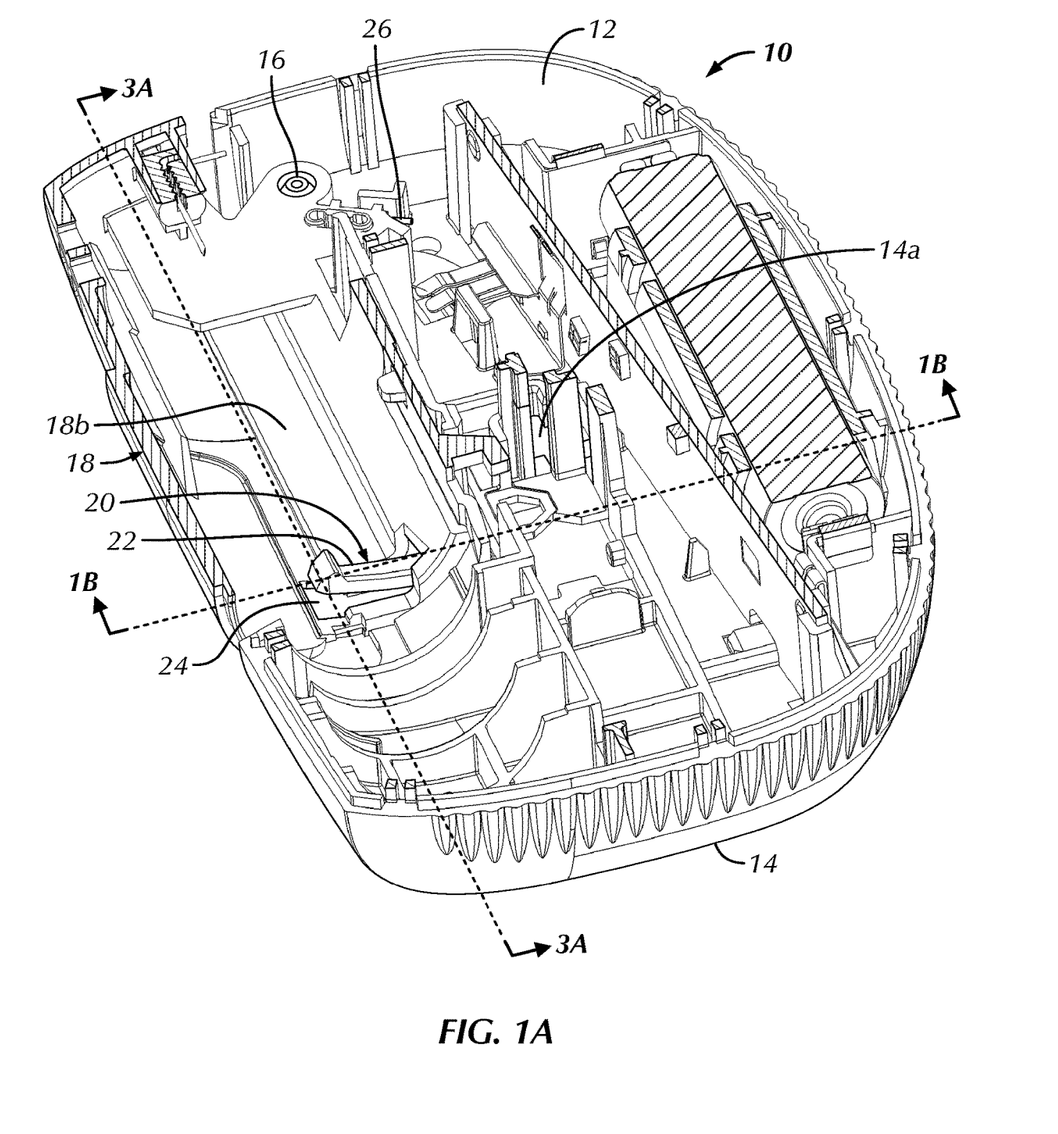
FIG. 1A is a top perspective view of a wearable injector, in accordance with an embodiment of the present disclosure, having a top surface of the injector removed, with an empty cartridge door oriented in a fully closed position thereof.
Figure 1B:
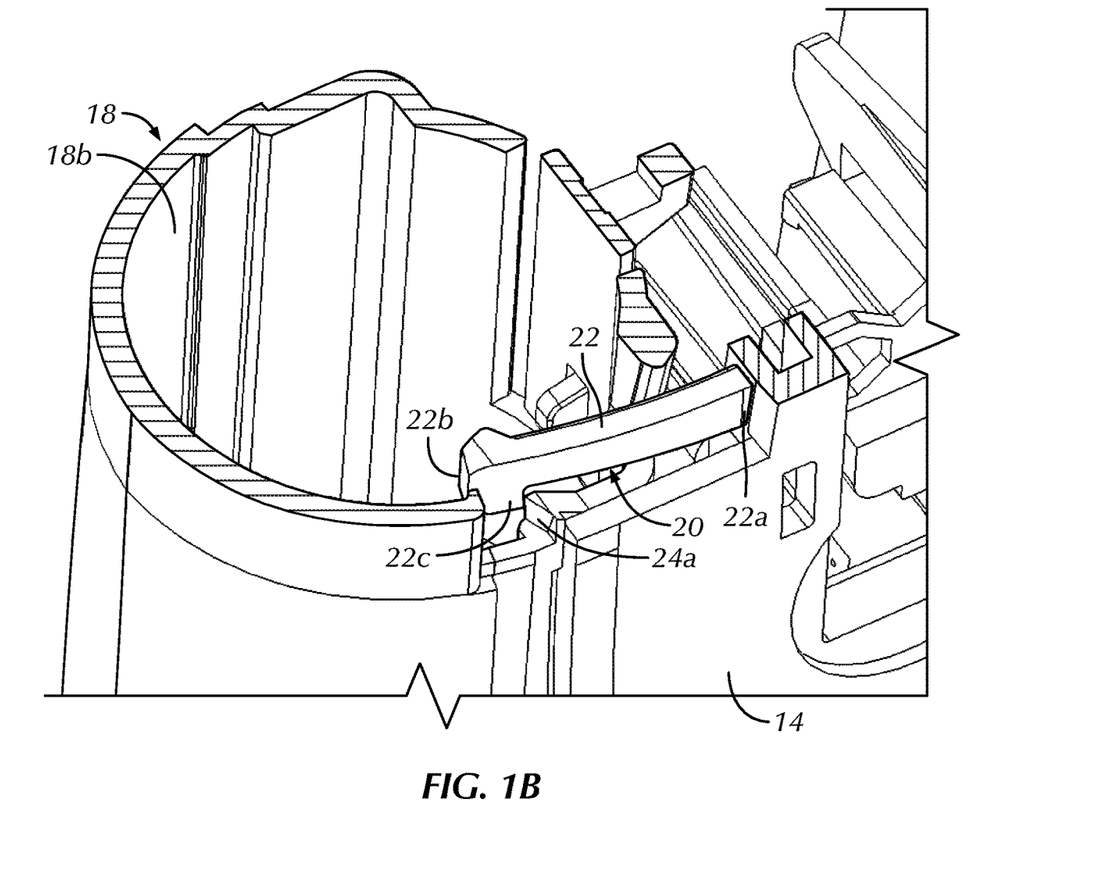
FIG. 1B is a partial cross-sectional view of the injector of FIG. 1A, taken along the sectional line 1B-1B of FIG. 1A, with the empty cartridge door in the fully closed position thereof and a latching mechanism of the injector in an unlatched position.
Figure 2:
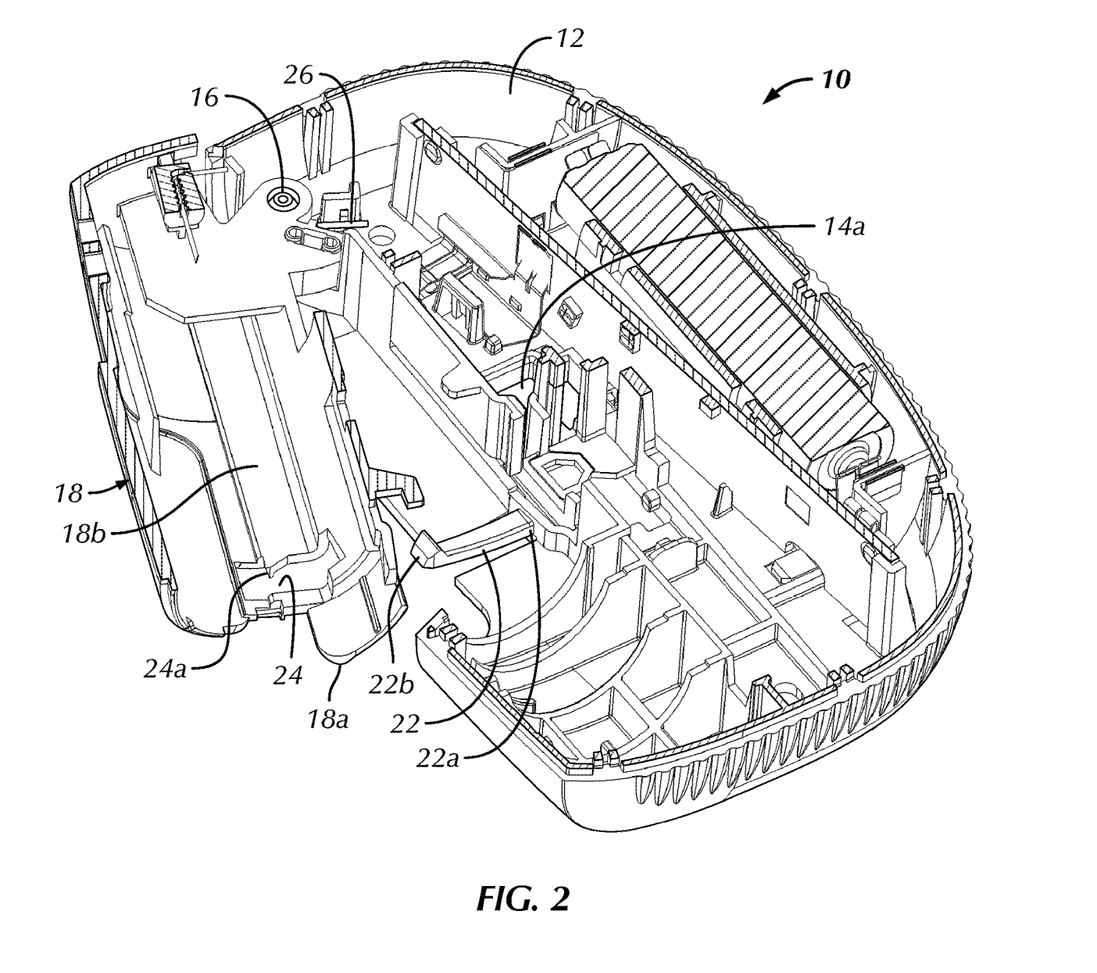
FIG. 2 is a top perspective view of the injector of FIG. 1A, having a top surface of the injector removed, with the empty cartridge door oriented in a fully open position thereof.

An injector door 18 is movably mounted to the injector housing 12 between a fully closed position (FIGS. 1A, 1B, 3A, 3B) and a fully open position (FIG. 2). The injector door 18 is openable to receive the cartridge 50 within the injector 10. In the illustrated embodiment, the injector door 18 takes the form of a cartridge door, but the disclosure is not so limited. The cartridge door 18 includes an open end 18a for receiving, e.g., slidably, the cartridge 50 therethrough, and defines an interior channel 18b therein to receive the cartridge 50. The interior channel 18b may be sized and shaped to receive and stabilize the cartridge 50 therein. Alternatively, the interior channel 18b may include a cartridge cradle, a cartridge track, individual stabilizing members, combinations thereof, or the like (not shown) to receive and stabilize the cartridge 50 in the interior channel 18b.

In an at least partially closed position of the cartridge door 18, such as the fully closed position of FIG. 1A, the interior channel 18b is not sufficiently accessible from outside of the injector housing 12 to insert a cartridge 50 therein. For example, the open end 18a of the cartridge door 18 is sufficiently obscured/covered by a portion of the injector housing 12 such that access to the interior channel 18b is prevented and the cartridge 50, therefore, cannot be inserted into the interior channel 18b. In the fully open position of the cartridge door 18 (FIG. 2), the open end 18a of the cartridge door 18 is sufficiently exposed/uncovered to permit insertion of the cartridge 18 therethrough and into the interior channel 18b.

In the illustrated embodiment, the cartridge door 18 is pivotably attached to the injector housing 12, e.g., via pin connection 16, proximate a closed, distal end of the interior channel 18b, opposite the open end 18a, but the disclosure is not so limited. As shown best in FIG. 1A, the cartridge door 18 is substantially flush with the exterior body of the injector housing 12 in the fully closed position. As shown in FIG. 2, the cartridge door 18 is pivoted away from the injector housing 12 in the open position, whereby the interior channel 18b is accessible from the open end 18a of the cartridge door 18. Other non-limiting examples of a cartridge door 18 movably mounted to an injector housing 12 are described in U.S. Patent Application Publication No. 2018/0152281, entitled, "Cartridge Insertion For Drug Delivery Device," the entire contents of which are incorporated by reference herein.

The injector 10 further includes a latching mechanism 20 movable between a latched position (FIGS. 3A, 3B), locking the cartridge door 18 to the injector housing 12 in the fully closed position of the cartridge door 18, and an unlatched position (FIGS. 1A, 1B, 2), unlocking the cartridge door 18 from the injector housing 12, thereby enabling movement of the cartridge door 18 from the closed position thereof toward the open position thereof (as will be described in further detail below). In the illustrated embodiment, the latching mechanism 20 includes an elastically deflectable, cantilevered arm 22 and a window 24 in the sidewall of the cartridge door 18, aligned with the cantilevered arm 22. As should be understood by those of ordinary skill in the art, the elastic deflection properties of the cantilevered arm 22 may be achieved via material properties, dimensions, a combination thereof, or the like. In one embodiment, the cantilevered arm 22 may be constructed of an elastically deflectable polymer, but the disclosure is not so limited. The cantilevered arm 22 extends from a fixed end 22a, attached to the injector housing 12, to a flanged, terminal, free end 22b. In some embodiments, the cantilevered arm 22 may be integrally formed, i.e., unitary and monolithic, with the injector housing 12. For example, the cantilevered arm 22 may take the form of a molded component of the injector housing 12. Alternatively, the cantilevered arm 22 may be separately formed and secured to the injector housing 12.

Figure 3A:
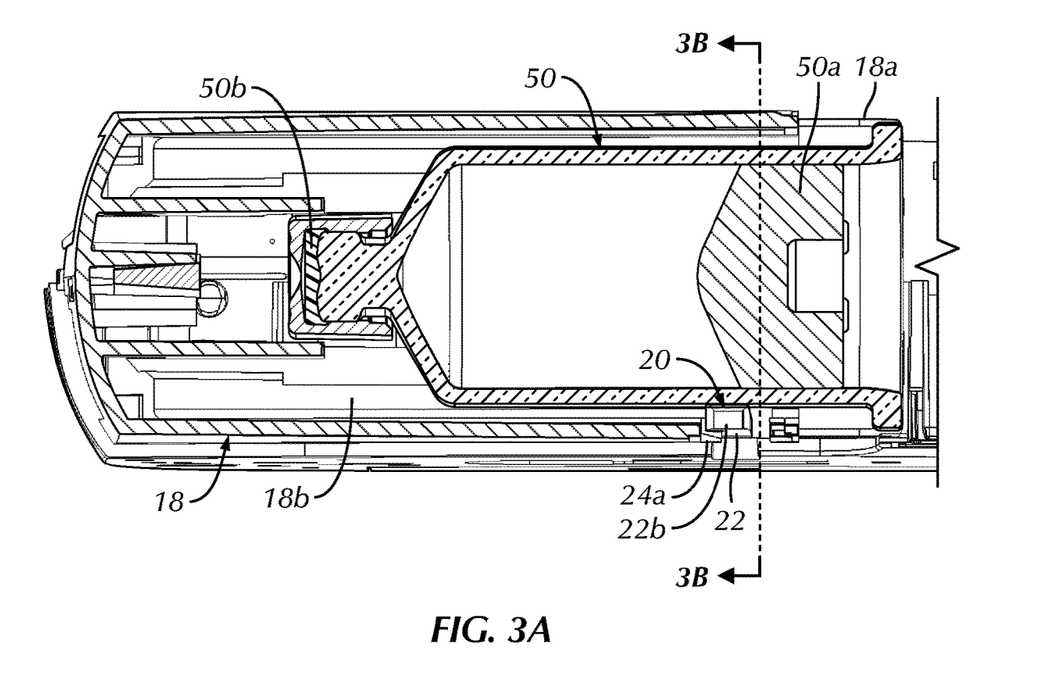
FIG. 3A is a partial cross-sectional view of the injector of FIG. 1A, taken along the sectional line 3A-3A of FIG. 1A, with a cartridge loaded in the cartridge door and the cartridge door oriented in the fully closed position thereof, thereby orienting the latching mechanism in a latched position thereof.
Figure 3B:
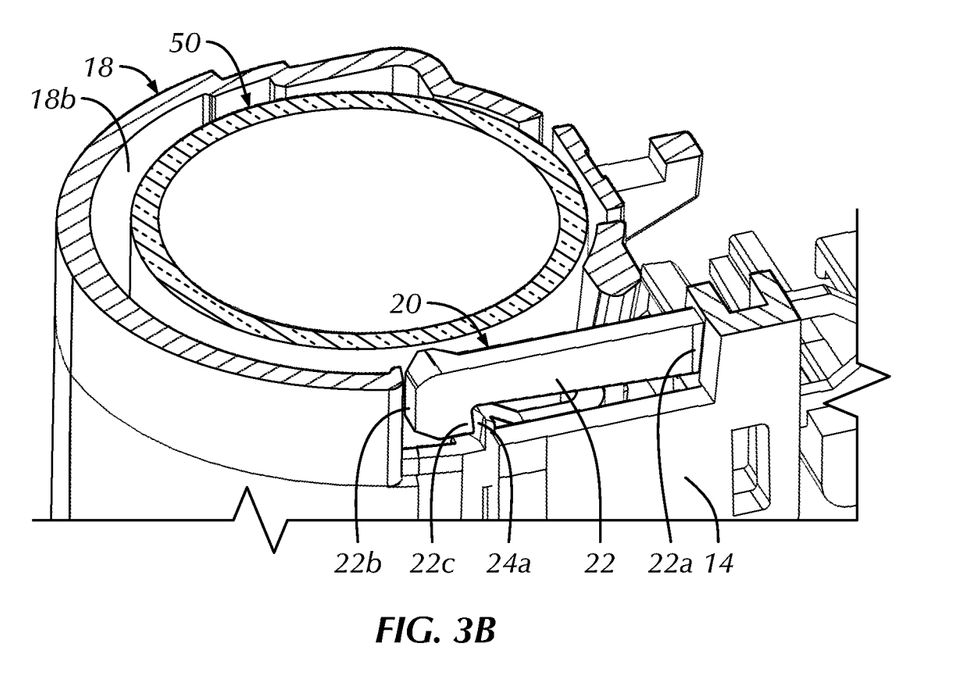
FIG. 3B is a partial cross-sectional view of the injector of FIG. 1A, taken along the sectional line 3B-3B of FIG. 3A.

As shown best in FIGS. 1B, 2 and 3B, a portion of the border of the window 24 defines a laterally inwardly projecting catch 24a, i.e., projecting inwardly into the aperture in the sidewall of the cartridge door 18 defined by the window 24. The terminal end 22b of the cantilevered arm 22 defines a corresponding and opposing lateral flange 22c facing the catch 24a. In the fully closed position of the cartridge door 18 (FIGS. 1A, 1B, 3A, 3B), the cantilevered arm 22 extends into the interior channel 18b of the cartridge door 18 through the window 24. In the fully open position of the cartridge door 18, the cantilevered arm 22 is withdrawn from the window 24 (FIG. 2). The cantilevered arm 22 is configured to have a natural, i.e., undeflected, position in which the cantilevered arm 22 is oriented in the unlatched position. That is, the terminal end 22b of the cantilevered arm 22, and, particularly, the flange 22c, is biased away, and disengaged from, the catch 24a. In illustrated embodiment, the cantilevered arm 22 is naturally biased upwardly in the undeflected position.

The cantilevered arm 22 remains undeflected when a cartridge 50 is not present in the interior channel 18b. In the fully closed position of the cartridge door 18, when the cartridge 50 is not present in the interior channel 18b of the cartridge door 18, i.e., the cartridge 50 has not yet been loaded in the interior channel 18b, the cantilevered arm 22 extends into the interior channel 18b of the cartridge door 18 through the window 24 (FIGS. 1A, 1B). Nevertheless, the latching mechanism 20 is oriented in the unlatched position thereof because there is no cartridge present within the interior channel 18b to deflect the flange 22c into engagement with the catch 24a. Thus, the cartridge door 18 will not lock when a cartridge 50 is not loaded therein despite being positioned in the closed position and remains movable between the open and closed positions thereof.

The latching mechanism 20 is configured to move to the latched position thereof solely when a cartridge 50 is present in the cartridge door 18 and the cartridge door 18 is subsequently moved to the fully closed position thereof (FIGS. 3A, 3B). That is, as shown in FIG. 2, when the cartridge door 18 is moved to the open position thereof, the cantilevered arm 22 is withdrawn from the window 24. When a cartridge 50 is inserted into the interior channel 18b of the open cartridge door 18 and the cartridge door 18 is subsequently moved to the closed position thereof, the window 24 once again receives the cantilevered arm 22 therethrough and into the interior channel 18b of the cartridge door 18. The presence of the cartridge 50 within the interior channel 18 deflects the flange 22c of the cantilevered arm 22 into engagement with the catch 24a.

For example, the curved sidewall of the cartridge 50 deflects the cantilevered arm 22 progressively downwardly as the cartridge door 18 is moved progressively further toward the fully closed position, until the flange 22c of the cantilevered arm 22 interlocks with the catch 24a of the window 24 when the cartridge door 18 reaches the fully closed position. In some embodiments, if another object, not having a smooth curved wall as the cartridge 50, is inserted into the interior channel 18b of the cartridge door, the object may collide against the terminal end 22b of the cantilevered arm 22, rather than deflect the cantilevered arm 22, thereby blocking the cartridge door 18 from reaching the fully closed position thereof.

In some embodiments, a biasing member 26 (FIG. 2) may be mounted in the injector housing 12 and configured to bias the cartridge door 18 toward the fully open position thereof. In the illustrated embodiment, the biasing member 26 takes the form of a torsion spring mounted between a non-movable member of the injector housing 12 and a member of the movable cartridge door 18, i.e., the torsion spring 26 abuts the injector housing 12 at one end thereof and abuts the cartridge door 18 at an opposing end thereof. In the closed position of the cartridge door 18, the torsion spring 26 is at least partially compressed, storing potential energy proportional to the amount of twisting thereof. When the torsion spring 26 is uninhibited (as will be described in further detail below), the torsion spring 26 expands, i.e., untwists, to move the cartridge door 18 toward the fully open position thereof. In the illustrated embodiment, the helical center of the torsion spring 26 is mounted around the pin connection 16, but may be otherwise positioned. As also should be understood by those of ordinary skill in the art, the biasing member 26 may alternatively take the form of other members capable of storing and releasing energy. Non-limiting examples include other springs (e.g., coil or leaf springs) and the like. Alternatively, a biasing member 26 may not be employed in the injector 10 and the cartridge door 18 may be manually movable between the fully closed position and the fully open position thereof.

Figure 4:
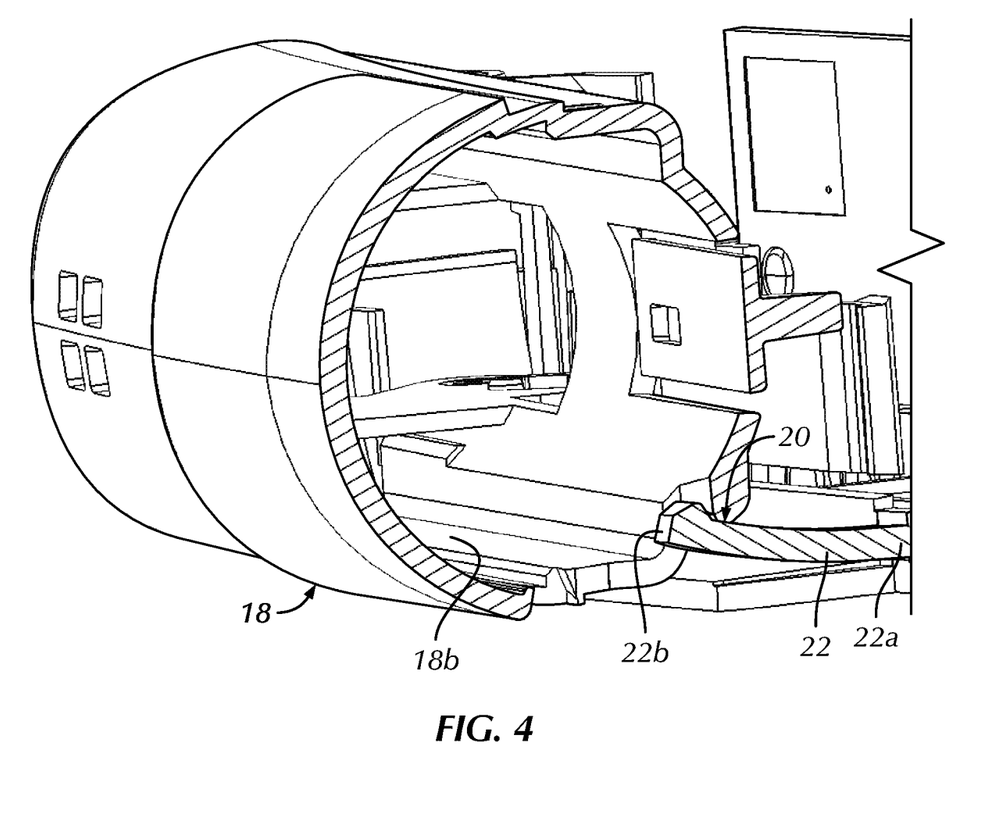
FIG. 4 is a perspective view of the cartridge door of the injector of FIG. 1A, with the cartridge door oriented in a partially open/partially closed position.

In some embodiments, as shown best in FIG. 4, the cantilevered arm 22 may be configured to also block the cartridge door 18 from reaching the fully open position thereof solely under the force of the biasing member 26. That is, the biasing member 26 biases the empty cartridge door 18 from the fully closed position (FIG. 1A), wherein the cantilevered arm 22 projects through the window 24 and into the interior channel 18b, toward the fully open position, wherein the cantilevered arm 22 is withdrawn from the window 24. Optionally, the natural, undeflected position of the cantilevered arm 22 defines a position wherein the terminal end 22b of cantilevered arm 22 catches onto another portion the window 24 (FIG. 4), e.g., a top head of the window 24, as the cantilevered arm 22 is being withdrawn from the window 24 during movement toward the fully open position, blocking further movement of the cartridge door 18 toward the fully open position thereof solely under the biasing force of the biasing member 26. The cartridge door 18, therefore, only reaches a partially open/partially closed position under the bias of the biasing member 26 (FIG. 4) until the terminal end 22b catches onto the window 24. The cantilevered arm 22, however, is deflectable out of engagement with the window 24, i.e., unlatching the flanged terminal end 22b from the window 24 upon application of a force toward the fully open position of the cartridge door 18 in addition to the biasing force of the biasing member 26, thereby enabling the cartridge door 18 to reach the fully open position thereof. For example, the terminal end 22b may define an inclined surface that faces and catches on the top head of the window 24. Accordingly, the terminal end 22b may deflect and slide out of engagement with the top head of the window 24 with an additional force is applied to the cartridge door 18 toward the fully open position thereof. For example, a user may manually pull the cartridge door 18 toward the fully open position thereof, to deflect the cantilevered arm 22 out of engagement with the window 24.

In use, the injector 10 may be initially delivered to a user with the cartridge door 18 in the fully closed position thereof. Where a biasing member 26 is employed, the injector 10 may be delivered to a user with the cartridge door 18 in a partially open/partially closed position, with the cantilevered arm 22 blocking the cartridge door 18 from reaching the fully open position. Alternatively, the injector 10 may be delivered to a user with the cartridge door 18 in the fully open position. Where the cartridge door 18 is fully or partially closed, a user pulls the cartridge door 18 to the fully open position thereof (FIG. 2) and inserts a cartridge 50 into the interior channel 18b. The user thereafter moves the cartridge door 18 to the fully closed position, whereby the flange 22c of the cantilevered arm 22 interlocks with the catch 24a of the window 24, as previously explained (FIGS. 3A, 3B). Accordingly, the cartridge door 18 locks in the fully closed position thereof with the cartridge 18 present therein. Advantageously, therefore, the cartridge door 18 will not lock in the fully closed position thereof unless a cartridge 50 has been inserted into the interior channel 18b. Should the empty cartridge door 18 be inadvertently moved into the fully closed position during delivery to the user, by the user prior to loading the cartridge 50, or at any other time without the cartridge 50 present therein, the cartridge door 18 will not lock (and the injector 10 will not be disabled) because the flange 22c of the cantilevered arm 22 will not interlock with the catch 24a of the window 24, as previously explained (FIG. 1A). Thus, the cartridge door 18 will remain movable into the open position thereof for loading of the cartridge 50.

It will be appreciated by those skilled in the art that changes could be made to the embodiments described above without departing from the broad inventive concept thereof. As one example, without limitation, the cantilevered arm 22 may alternatively extend from the cartridge door 18, and the window 24 defining the catch 24a may be formed in the injector housing 12. It is understood, therefore, that this invention is not limited to the particular embodiments disclosed, but it is intended to cover modifications within the spirit and scope of the present invention, as set forth in the appended claims.

We claim:

1. An injector configured to receive therein a cartridge containing a substance to be dispensed, the injector comprising:
   an injector housing;
   a cartridge door movably mounted to the injector housing and having an open end and an interior channel to load the cartridge therein through the open end, the cartridge door being movable between a fully closed position, wherein the open end is obscured by the injector housing to prevent insertion of the cartridge into the interior channel, and an open position, wherein the open end is sufficiently exposed to receive the cartridge therethrough and into the interior channel; and
   a latching mechanism movable between a latched position, locking the cartridge door to the injector housing in the fully closed position thereof, and an unlatched position, unlocking the cartridge door from the injector housing, thereby enabling movement of the cartridge door toward the open position,
   wherein the latching mechanism is oriented in the unlatched position when the cartridge door is empty and a portion of the latching mechanism is engaged with the cartridge to move the latching mechanism to the latched position when a cartridge is present in the cartridge door and the cartridge door is subsequently moved to the fully closed position thereof.

2. The injector of claim 1, wherein the latching mechanism comprises an elastically deflectable, cantilevered arm and an opposing catch, the cantilevered arm being disengaged from the catch in the unlatched position and the cantilevered arm being configured to be deflected to interlock with the catch in the latched position.

3. The injector of claim 2, wherein one of the injector housing and the cartridge door includes the cantilevered arm, and another of the injector housing and the cartridge door includes the opposing catch.

4. The injector of claim 2, wherein the cartridge door includes a window in a sidewall thereof and the catch forms a portion of the window, the cantilevered arm projecting through the window and into the interior chamber of the cartridge door in the fully closed position thereof, the cantilevered arm comprising a flanged, terminal end configured to interlock with the catch when the cartridge is present in the cartridge door and the cartridge door is subsequently moved to the fully closed position thereof.

5. The injector of claim 2, wherein the cantilevered arm is configured to be deflected by the cartridge present in the cartridge door.

6. The injector of claim 2, wherein the cantilevered arm is undeflected in the unlatched position.

7. The injector of claim 1, further comprising a biasing member applying a biasing force upon the cartridge door, thereby biasing the cartridge door toward the open position thereof.

* * * * *